United States Patent [19]

Fleisher

[11] Patent Number: 5,641,489
[45] Date of Patent: *Jun. 24, 1997

[54] EXTRACTING MALTOL AND WATER FROM NATURALLY OCCURRING PLANT MATERIAL CONTAINING MALTOL AND WATER

[75] Inventor: Alexander Fleisher, Wayne, N.J.

[73] Assignee: Florasynth Inc., Teterboro, N.J.

[*] Notice: The term of this patent shall not extend beyond the expiration date of Pat. No. 5,441,612.

[21] Appl. No.: 517,647

[22] Filed: Aug. 22, 1995

Related U.S. Application Data

[63] Continuation of Ser. No. 192,126, Feb. 3, 1994, abandoned.

[51] Int. Cl.$^6$ ............................................. A61K 35/78
[52] U.S. Cl. .......................... 424/195.1; 424/196.1; 514/783
[58] Field of Search .................. 424/195.1, 196.1; 514/783

[56] References Cited

U.S. PATENT DOCUMENTS

| | | | |
|---|---|---|---|
| 3,501,501 | 3/1970 | Heintz et al. | |
| 4,284,657 | 8/1981 | Stanton | 426/651 |
| 5,120,558 | 6/1992 | Nguyen et al. | 426/425 |
| 5,221,756 | 6/1993 | Fleisher et al. | 549/418 |
| 5,240,464 | 8/1993 | Kluger et al. | 8/506 |
| 5,275,950 | 1/1994 | Dickman et al. | 435/280 |
| 5,296,621 | 3/1994 | Roos et al. | 554/15 |
| 5,332,742 | 7/1994 | Rosenberg | 514/253 |
| 5,342,973 | 8/1994 | Becker et al. | 549/534 |
| 5,441,612 | 8/1995 | Fleisher et al. | 204/157.15 |

FOREIGN PATENT DOCUMENTS 9529908  11/1995  WIPO .

OTHER PUBLICATIONS

Fleisher and Fleisher (1991) "Water–Soluble Fractions of the Essential Oils", *Perfumer and Flavorist* 16:37–41.

Goos and Reiter (1946) "New Products from Wood Carbonization", *Industrial and Engineering Chemistry* 38(2):132–135.

LeBlanc and Akers (1989) "Maltol and Ethyl Maltol: From the Larch Tree to Successful Food Additive", *Food Technology*, pp. 78–84.

Fleisher, A. (1990) "The Poroplast Extraction Technique in the Flavor and Fragrance Industry", *Perfumer and Flavorist* 15(5):27–36.

*Primary Examiner*—John Kight
*Assistant Examiner*—Howard C. Lee
*Attorney, Agent, or Firm*—Scully, Scott, Murphy & Presser

[57] ABSTRACT

Disclosed is a method for recovering maltol and water from naturally occurring plant material containing maltol and water. The maltol is extracted by utilizing a water-immiscible extractant while simultaneously stripping water from the plant material.

5 Claims, 1 Drawing Sheet

EXTRACTING MALTOL AND WATER FROM NATURALLY OCCURRING PLANT MATERIAL CONTAINING MALTOL AND WATER

This is a continuation of application Ser. No. 08/192,126 filed on Feb. 3, 1994, now abandoned.

BACKGROUND OF THE INVENTION

The present invention generally relates to the recovery of odoriferous principles from plant material by solvent extraction. More specifically, it relates to preparation of oleoresins from fresh plant material and even more specifically to the solvent extraction of the fresh foliage of coniferous trees.

In particular, this invention relates to the recovery of aromatic resin from fresh foliage of coniferous evergreens which contain substantial quantities of maltol (2-methyl-3-hydroxy-4-pyrone). Maltol is a heterocyclic aromatic chemical used extensively in flavor and fragrance compositions. The resin obtained by the process described in the present invention can be used as an ingredient in flavor or fragrance compositions or as a commercial source for the recovery of natural maltol.

The recovery of aromatic principles from plant material through solvent extraction has in the past been achieved using materials such as olive oil and various liquid fats as well as wine, and in more modern times using a variety of solvents such as ethyl alcohol, acetone, hexane and petroleum ether.

Hundreds of botanical species are used as raw materials and in each case a particular part of the plant such as leaves, stems, bark, fruit or flowers are found to be most suitable. Despite the variety of plant sources and the multitude of solvents that can be used in the extraction process, all known methods have one common basis. This is a preferential solubility and affinity of the aroma determining substances for the chosen solvent. The process of extraction is, in fact, preferable diffusion of aroma carrying chemicals from the plant material into a solvent phase. The chemicals can be concentrated and recovered from the solvent phase by stripping, usually through a distillation process.

Numerous extraction means used for contacting plant material with the solvent are designed to speed up and intensify the diffusion process. Despite the multitude of botanical sources and known extraction techniques, they can be divided into two major groups—those which use dehydrated plant material and those in which the oleoresin is extracted from fresh plant tissues. Cinnamon bark, black pepper, various fruits of the Umbelliferae family such as cumin, caraway, celery, etc. can be used as examples of plant material which is extracted dry. Rose flowers, jasmine, tuberose and lavender are examples of plant material which is extracted fresh.

Hardy raw materials which are mentioned in the first group usually retain their aromatic values through the dehydration process, while gentle tissues of flowers generally completely surrender their aromatic principals. The dehydration process alters the cell structure of the plant tissue, creating pores and cavities accessible to solvents and thus making the diffusion process reasonably quick. The plant material extracted fresh usually consists of flowers with gentle and thin petals which, despite the presence of water, offers low resistance to the diffusion.

The difficulty in conducting the extraction process becomes rather severe when hardy plant material is to be extracted but the aromatic values do not survive dehydration. Such is the case of a variety of coniferous plants and, in particular, various species of fir. The needles of the fir trees are specifically adapted to a very low rate of water evaporation therefrom and offer hard resistance to the penetration of the solvent. Thus, simple contact of fir needles with solvents results in very slow extraction. Due to the specific shape of the needles, a rough grinding is not efficient either, since breaking of the needle exposes only a small cross section to solvent penetration. It is, of course, possible to grind or to disperse fir needles into very fine particles. Such a process, however, is very expensive and for many reasons impractical.

The oleoresins of the coniferous trees are well known in the flavor, fragrance, cosmetic and pharmaceutical industries. The resin extracted from balsam fir (*Abias balsamea L.*) is the most widely known, and is even allowed to be used in food.

The presence of maltol in the coniferous trees in general, and in the balsam fir specifically, is well established in scientific literature. Maltol has also been reported to be in the bark of some species of larch trees. Maltol is present in latch bark in combined form to an extent varying from about 0.1 percent to about 2 percent by weight depending upon the bark layer and the season of harvest. The richest supply of maltol is found in the bark of roots of the larch trees although, for practical reasons, not much root bark is harvested. Large quantities of larch trees and bark containing maltol exist and are available primarily in the northwest part of the United States and southwest Canada. The bark is available at sawmills where it is stripped off of larch trees and stored in a pile, there to be burned for fuel or otherwise used if economical processes for recovering useful components therefrom can be found.

Limited quantities of fir balsam oleoresin are steadily produced by the extraction of dehydrated fir needles. The yield of oleoresin is rather low and so is the maltol content in it. The product is, therefore, costly and usually is employed only in expensive flavor and fragrance compositions. Due to its high cost and the low content of maltol, fir balsam oleoresin has not been seriously considered to be a practical source for recovery of maltol. Indeed, dehydration of the fir needles causes loss of essential oils, substantial reduction in the yield of oleoresin and a severe decrease in the maltol content of the product which is thereafter recovered. This result has been demonstrated by the applicant.

Despite the attractiveness of maltol and of oleoresins containing maltol, recovering significant amounts of maltol using known extraction techniques has proven to be difficult or disappointing.

Maltol is insoluble in non-polar hydrocarbons, which renders solvent extraction with such solvents unsuitable for recovering maltol-containing resin from plant material. Although maltol is soluble in hot water, the data in scientific and patent literature indicates that maltol cannot be efficiently recovered from plant material by hot water extraction.

Maltol shows substantial solubility in polar solvents such as acetone, alcohol, and the like. However, these solvents are water soluble and will dissolve not only maltol but also all the water contained in the fresh plant source material. This property makes subsequent recovery of the oleoresin or the maltol a difficult task. Utilization of water immiscible solvents (in which maltol is still soluble) for the extraction of fresh plant material by conventional techniques is restricted by the presence of water as described above.

Thus, there still remains a need for a method for recovering oleoresin, particularly maltol-containing oleoresin, from a source which is plant material.

It is an object of the invention to overcome the obstacles in recovery of oleoresins from source material including fresh plant material, and in particular from the foliage of coniferous species. It is a particular object of this invention to permit the removal of oleoresins, and particularly those containing maltol, from source material including plant material.

BRIEF SUMMARY OF THE INVENTION

In one aspect, the present invention is a method for removing oleoresin from hydrous source material containing said oleoresin, comprising extracting said source material with a water-immiscible extractant in which said oleoresin is soluble to form a solution of said oleoresin in said extractant while simultaneously stripping water from said source material and volatilizing said water to form a vapor comprising said water and said extractant.

The solution of extractant and oleoresin is recovered for further treatment to obtain the oleoresin or desired fraction thereof.

In a preferred aspect of this invention, the extractant is recovered from the solution and/or the vapor and is recycled to the extracting step.

DETAILED DESCRIPTION OF THE INVENTION

Figure 1:
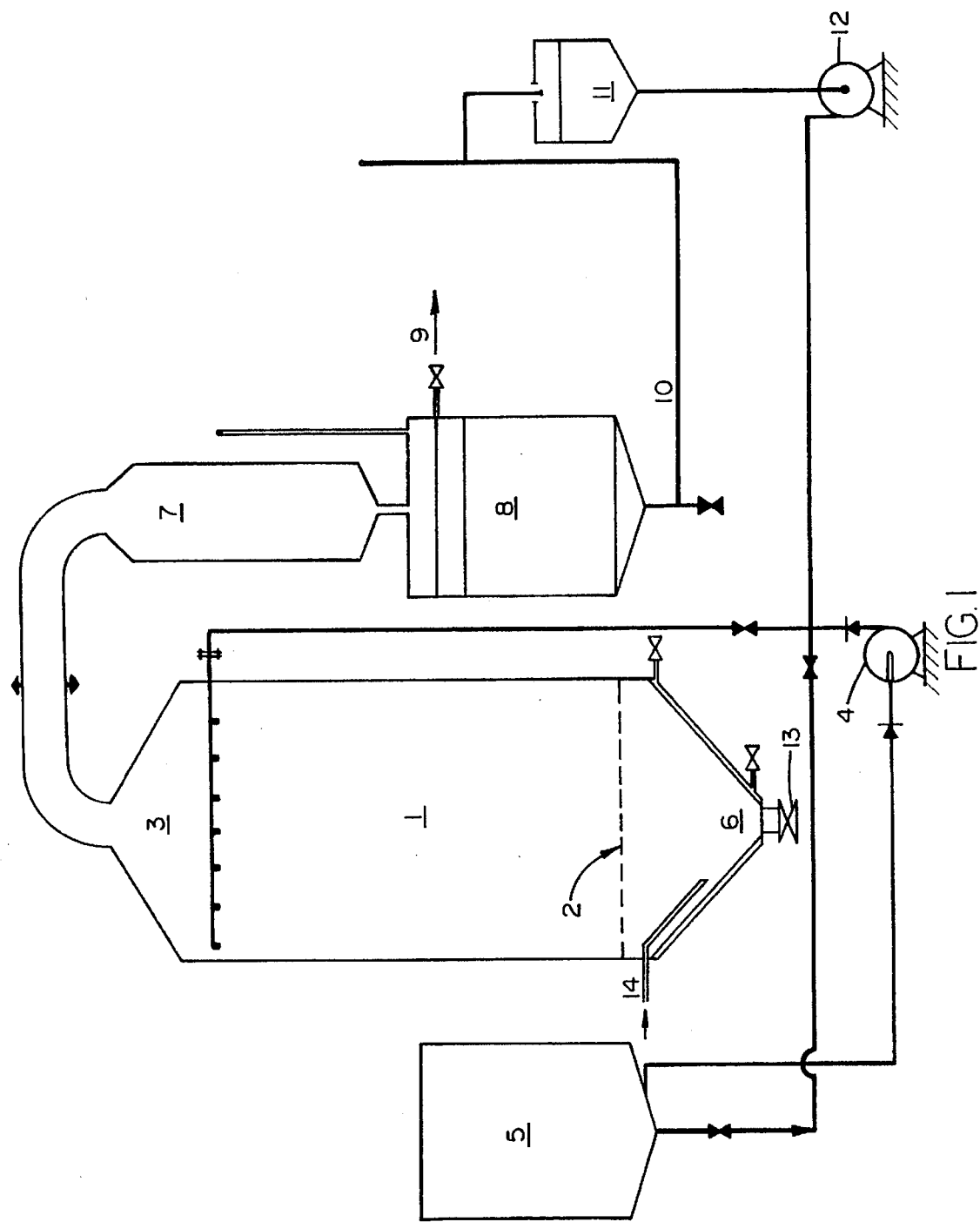
FIG. 1 is a flow chart of a preferred embodiment of the method of the present invention.

The present invention is useful for treating source material that is hydrous, by which is meant source material that contains water. The source material can, of course, be solid, yet hydrous; a preferred example of such source material is fresh (that is, not totally dehydrated) plant materials such as needles, leaves, bark, branches and other plant tissue. A particularly preferred hydrous source material is fir foliage, in particular balsam fir foliage, including needles and small branches. Another preferred source is larch foliage or bark. The moisture content of hydrous source material treated in accordance with the method of the present invention can range from on the order of 1 wt. % up to 10 wt % and even higher, that is, up to 50 wt. % moisture content or higher.

The method of the present invention is useful in removing oleoresin from such hydrous source material. The oleoresin is generally comprised of one or more organic aromatic principles, a particularly preferred example of which is maltol. The "oleoresin" which is removed from hydrous source material by the method of the present invention may comprise all resinous components present or a desired fraction thereof.

In the method of the present invention, the hydrous source material is subjected to a simultaneous extracting and stripping step in which the source material is contacted with an extractant. It is not necessary to subdivide the hydrous source material to any particularly fine particle size, although it will be recognized that, depending on the form of the source material, some reduction in size may be appropriate if an improvement in the extracting and stripping efficiency or yield can be afforded without encountering increased difficulties in material handling.

A desirable extractant will comprise a compound, or a mixture of compounds, characterized in that the oleoresin (which term as used herein incorporates portions of oleoresin present which are desired to be removed from the source material) is soluble in the extractant. Preferably, the solubility of the oleoresin in the extractant exceeds its solubility in water at the temperatures at which the process is carried out.

The extractant should be water-immiscible in the sense that a mixture of water and the extractant should form upon standing two separate phases within a reasonable length of time generally on the order of about a minute. Minor solubility of water in the extractant, or of the extractant in water, generally on the order of up to about 1 wt. %, can be tolerated without departing from the objectives of the present invention. It will be recognized, however, that the efficiency and yield of the method of the present invention may be affected to the extent that water is soluble in the extractant or that the extractant is soluble in water.

The extractant also needs to be capable of assisting the stripping of the moisture content from the hydrous source material to form a vapor comprising the extractant and the stripped water. Thus, extractants having a boiling point between 20° C. and 100° C. are useful, as well as other extractants having a significant vapor pressure at 100° C. (i.e., the boiling point of water).

In addition, the extractant needs to be incapable of causing the oleoresin desired to be extracted from undergoing chemical change in structure either by reaction with the extractant or otherwise.

One extractant which has been found to be useful in the method of the present invention is 1,1,1-trichloroethane. Another extractant useful in these applications is trichloroethylene. These compounds are particularly useful in recovering an oleoresin fraction comprising maltol from balsam fir source material. Other extractants meeting the foregoing characteristics can readily be ascertained by the practitioner as determined by the characteristics of the particular hydrous source material to be treated and the particular oleoresin fraction desired to be recovered.

The extracting and stripping itself can be carried out in any of several different manners. In one embodiment, the hydrous source material is intimately contacted with the extractant in its vapor phase. For instance, the source material is held in a closed chamber to which a vapor of the extractant is fed in a manner which affords intimate contact between the extractant and the material. In another embodiment, the extractant is provided as a liquid which is boiled while the hydrous source material is immersed therein. In either embodiment, the amount of extractant relative to the amount of the hydrous source material having a given moisture content and the length of time through which the extractant remains in contact with the hydrous source material are adjusted to ensure that the gaseous extractant is able to carry with it water vapor stripped from the source material.

Preferably, the extracting-stripping conditions are adjusted so that the amount of oleoresin extracted from the hydrous source material is maximized, although it will be recognized that the amount of oleoresin remaining in the source material to be extracted therefrom may decline to a point where continued extracting requires amounts of extractant and additional time which make further extraction inefficient.

The extracting and stripping step can be carried out on a batch-wise or continuous basis, bearing in mind that it is necessary to feed fresh hydrous source material periodically or continuously and also to remove stripped source material.

The extraction and stripping is carried out at a temperature sufficient to strip water from the source material and to volatilize that water with a certain portion of the extractant.

The extraction forms a solution of the desired oleoresin in the extractant. If the extraction is carried out in liquid (boiling) extractant, the solution can remain in contact with the source material to be decanted or drained off subsequently or continuously. If the extraction is carried out by contacting extractant vapor with the source material (it being understood that the vapor may, in fact, condense on the surfaces of the material), the solution that forms can be allowed to drain off of the source material to be collected and removed from the apparatus concurrently or subsequently.

The oleoresin-rich product stream recovered from the extraction/stripping comprises a useful source of the desired oleoresin fraction. The extractant can be evaporated away, leaving a concentrated oleoresin fraction which can be used as such in the formulation of products such as, for example, personal care cosmetic products. However, this product stream can also be treated as is, or following further concentration or even complete removal of the extractant, to recover any particularly desired component fraction or compound, such as maltol.

For the recovery of maltol, following partial concentration of the extractant solution (to e.g. about 30% solvent), the concentrated extract can then be sequentially extracted with three portions of hot water at a 2:1 volume ratio (water:extract). The liquid phases separate easily on standing, whereupon the aqueous phases which contain maltol are combined and filtered, and the maltol can be recovered by extraction with methylene chloride using e.g. the "Poroplast" method described in A. Fleisher, "The Poroplast Extraction Technique in the Flavor and Fragrance Industry," *Perfumes and Flavorist* 15(5): 27–36 (1990). The solvent is stripped to provide crude maltol which can be recrystallized from 90% aqueous methanol which contains a small amount of EDTA.

The stripping step also forms a vapor stream comprising the extractant and water vapor. The water vapor is derived from the moisture content of the source material and preferably comprises all of the moisture content that is stripped from the source material. In the method of the present invention, this vapor stream is drawn away from the source material and is there condensed to form a liquid product comprising the extractant and water. This condensing step can be carried out in any conventional industrial condensing unit capable of cooling the vapor to ensure essentially complete condensation of the extractant and the water.

Next, the condensed extractant and water are recovered separately as separate product streams. This separation is advantageously carried out in any conventional holding tank, which may even be part of the apparatus used for condensing the stripped vapors. The separation process takes advantage of the immiscibility of the stripping agent and water for each other.

The extractant stream that is thus recovered can be recycled to the extracting-stripping step. This feature affords the operator the opportunity to minimize the cost of introducing fresh extractant into the method. This feature also minimizes the burden of disposing of spent extractant. The extractant may advantageously first be treated to remove therefrom any residual amounts of extracted oleoresin or other extracted material. This can conveniently be carried out by evaporating and recondensing the extractant and recovering separately any residue left behind upon the evaporation.

Referring to the accompanying FIGURE, tank 1 is an enclosed vessel having a perforated plate 2 near its lower end and an exit passageway 3 at its top.

Plant material is loaded into tank 1 onto perforated plate 2. A sufficient amount of extractant is pumped by pump 4 from a reservoir 5 and accumulates in the bottom 6 of the tank where it is evaporated by heating means (such as a heating coil). The rising vapors of the extractant contact the plant material. A portion of the extractant carries water vapor out through passageway 3 as a vapor stream. Substantial quantities of extractant also condense on the surface of the plant material providing a thin layer of the extractant.

The vapor stream leaving through passageway 3 passes into condenser 7 wherein it forms a liquid condensate which falls into separator 8 from which the water phase is removed as stream 9 for purification and discharge. The condensed extractant is removed as stream 10 into receiver 11 from which it is periodically pumped by pump 12 to the top of tank 1 where it washes down the extract which is formed on the surface of the plant material.

When the extraction is completed (as can be determined experimentally, for instance, by the reduction of the moisture content of the source material or by the oleoresin content of the solution), the concentrated resin solution in the extractant is discharged from area 6 of the tank through valve 13 for further purification. Residual extractant retained by the plant material can be removed by passing water steam 14 into the tank so as to pass through the plant material. Steam passing through the plant material removes the extractant with water. The extractant and water phases go through the condenser, separator and receiver. However, in this case the extractant is not returned to the extraction tank but is pumped into the pure fresh extractant reservoir 5.

The invention will be described further with reference to the following examples, which are intended for purposes of illustration and should not be construed as limiting the scope of this invention.

In the following examples, the yield of essential oil and the resin are given based upon absolutely dry weight.

Fir foliage that was dehydrated before use in the following examples had been previously dried for several days (air drying at 30° C.) to a residual humidity of 10%.

EXAMPLE 1

As one example of the method of the present invention, 200 grams of fresh balsam fir needles (*Abias balsamea L.*, 45.7% moisture content, collected in Eastern Quebec, Canada) were placed in a flask connecting to a water trap and a reflux condenser. 750 milliliters of 1,1,1-trichloroethane was added to the flask. The content of the flask was boiled on a water bath for 2.5 hours during which 90 milliliters of water was separated. The material temperature was initially 65° C. (the constant boiling point of the two-phase 1,1,1-trichloroethane-water system at atmospheric pressure) and eventually rose to 73° C. (about the boiling point of 1,1,1-trichloroethane). Upon completion of water separation, the trichloroethane extract was filtered from the plant material. The residual plant material was rinsed with additional 350 milliliters of trichloroethane and filtered again. The filtrates were combined and the solvent stripped to a constant weight under slightly reduced pressure. The yield of the resin was found to be 8%, and the content of maltol in the resin was 15.8%.

EXAMPLE 2

Fresh branches of balsam fir were harvested in upstate New York, USA. Maximum diameter of the woody parts was 0.5" or less.

The fresh needles were carefully separated from the woody parts, and their weight ratio was found to be 56% needles and 44% wood. The moisture content of the needles was found to be 54.3% and the branches was 52.1%.

The fresh needles and woody parts were subjected separately to extraction with 1,1,1-trichloroethane as described in Example 1.

The extraction of pure needles showed a yield of 8.1% resin (absolutely dry weight basis) while the maltol content was 16.4%. The extraction of branches resulted in 4.8% resin yield which contained only 2.4% maltol. Comparison of maltol content in the needles 1.4% (absolutely dry weight basis) vs. 0.1% in the branches shows that the branches represent undesirable ballast in the recovery of resin for maltol production.

EXAMPLE 3

The experiment described in Example 1 was repeated using trichloroethylene as the solvent. During 3.5 hours of the experiment, 89 milliliters of water was separated, and the temperature rose from an initial 74° C. to a final 85° C. The yield of the resin was found to be 4.2% (7.7% on absolute dry weight basis), and the maltol content in the resin was 23.9%.

EXAMPLE 4

100 grams of fresh needles were loaded into a glass container, the bottom of which was attached to a heated one-half liter flask, and the top of which was attached to a water trap and a reflux condenser. 100 milliliters of trichloroethylene was placed in the flask and boiled for 3.5 hours on a water bath. During this time 45.5 milliliters of water was separated. At the end of this period, the flask was disconnected and the solvent stripped under slightly reduced pressure.

The yield of the resin was found to be 7.5% (on absolutely dry weight basis) and the maltol content was 18%.

EXAMPLE 5

By contrast with the present invention, extractions were run using two other extraction regimens. The results showed that the present invention obtains superior yield.

A. Solvent Extraction—Maceration 200 grams of fresh fir needles were placed in the flask and mechanically stirred with 750 milliliters of 1,1,1-trichloroethane at a temperature of 64° C. (below the boiling point) for the same period of 2.5 hours. At the end of this period, the material was treated exactly as in Example 1 above. The yield of the resin was found to be 4.5%, and the maltol content was 19.8%.

Theoretical yield of maltol was found to be 1.26% through extraction via the present invention vs. 0.89% through this maceration process. If the hot maceration process is taken as a base for comparison, the use of the extraction method of the present invention results in an over 40% increase in the yield of maltol.

B. Extraction of Dry Needles

The essential oil content in these needles was found to be 1.85% vs. 2.4% in the fresh plant material.

100 grams of dehydrated needles were placed in a flask. 750 milliliters of 1,1,1-trichloroethane was added, and the content of the flask was refluxed for 2.5 hours. Solvent extract was filtered out, and the plant material was rinsed with additional 350 milliliters of trichloroethane. After combining of filtrate and stripping of the solvent, 4% resin yield was obtained which contained 7.2% of maltol. In comparison with the extraction and stripping of hydrous source material in accordance with the present invention. The theoretical yield of maltol shows a more than four fold decrease as a result of the dehydration process.

What is claimed is:

1. A method for removing maltol and water from naturally occurring plant material containing said maltol and water, comprising
   (A) contacting said material with a water-immiscible extractant in which extractant said maltol is soluble and simultaneously volatilizing water from said material, by either (A.1) contacting said material with said extractant while said extractant is a boiling liquid, or (A.2) contacting said material with vapor of said extractant and condensing a portion of said vapor to liquid on the surface of said material,
   wherein said step (A.1) or (A.2) is carried out under conditions wherein said maltol is extracted into solution in said liquid extractant and said water is volatilized from said material;
   (B) recovering said solution of maltol in said liquid extractant; and
   (C) removing said water as a product vapor comprising said water and a portion of said extractant.

2. The method of claim 1 wherein said plant material comprises balsam fir foliage.

3. The method of claim 1 which further comprises condensing extractant from said vapor and recycling said condensed extractant to said extracting step.

4. The method of claim 1 wherein said extractant is selected from the group consisting of trichloroethylene, 1,1,1-trichloroethane and mixtures thereof.

5. The method of claim 1 which further comprises recovering said oleoresin from said solution.

* * * * *